United States Patent [19]

Kormány et al.

[11] 4,014,871

[45] Mar. 29, 1977

[54] STILBENE COMPOUNDS

[75] Inventors: Géza Kormány, Allschwil; Guglielmo Kabas, Aesch; Hans Schläpfer; Adolf Emil Siegrist, both of Basel, all of Switzerland

[73] Assignee: Ciba-Geigy Corporation, Ardsley, N.Y.

[22] Filed: Aug. 6, 1975

[21] Appl. No.: 601,882

[30] Foreign Application Priority Data

Aug. 14, 1974 Switzerland .................... 11109/74

[52] U.S. Cl. .................. 260/240 C; 204/158 R; 252/301.17; 252/301.22; 252/301.24; 260/307 G; 260/308 A
[51] Int. Cl.² ................................ C07D 413/10
[58] Field of Search ............ 260/240 C; 204/158 R

[56] References Cited

UNITED STATES PATENTS

| | | | |
|---|---|---|---|
| 3,697,513 | 10/1972 | Siegrist | 260/240 D |
| 3,725,395 | 4/1973 | Siegrist | 260/240 CA |
| 3,732,221 | 5/1973 | Siegrist | 260/240 C |
| 3,779,931 | 12/1973 | Fries et al. | 260/240 C |
| 3,796,705 | 3/1974 | Siegrist | 260/240 C |
| 3,830,848 | 8/1974 | Siegrist | 260/240 CA |

OTHER PUBLICATIONS

Siegrist (VI), Helv. Chim. Acta 57(1), 1974, pp. 81–84, 88, 93, 100, 101.

*Primary Examiner*—Arthur P. Demers
*Attorney, Agent, or Firm*—Joseph G. Kolodny; Edward McC. Roberts; Prabodh I. Almaula

[57] ABSTRACT

Stilbene compounds of the formula

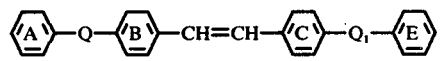

wherein Q denotes the 1,3,4-oxadiazol-2,5-ylene or 1,2,4-oxadiazol-3,5-ylene radical and $Q_1$ denotes one of the radicals

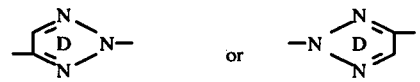

and the rings A, B, C, D and E can each contain 1 to 3 non-chromophoric substituents.

12 Claims, No Drawings

STILBENE COMPOUNDS

The present invention relates to new stilbene compounds, processes for their manufacture and their use for the optical brightening of high molecular organic materials.

The new stilbene compounds correspond to the formula

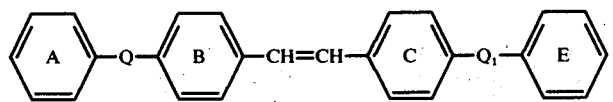

(1)

wherein Q denotes the 1,3,4-oxadiazol-2,5-ylene or 1,2,4-oxadiazol-3,5-ylene radical and $Q_1$ denotes one of the radicals

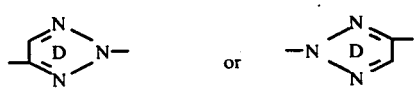

and the rings A, B, C, D and E can each contain 1 to 3 non-chromophoric substituents.

Accordingly, the formula (1) comprises compounds of the formulae

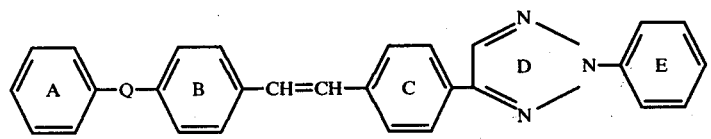

(2)

and

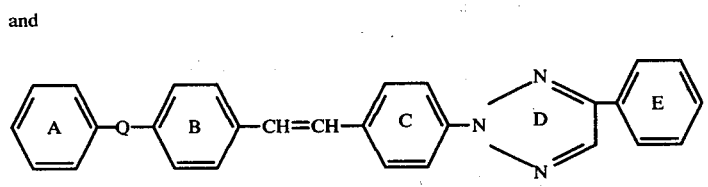

(3)

wherein Q and the rings A, B, C, D and E have the above-mentioned meaning.

Non-chromophoric substituents are, for example, alkyl with 1 to 12 carbon atoms, cyclohexyl, phenylalkyl with 1 to 3 carbon atoms in the alkyl part, unsubstitued phenyl or phenyl substituted by 1 or 2 substituents from the series chlorine, methyl or methoxy, alkoxy with 1 to 4 carbon atoms, unsubstitued phenoxy or phenoxy substituted by 1 or 2 substituents from the series chlorine, methyl or methoxy, chlorine, fluorine, bromine, cyano, —COOR, wherein R represents hydrogen, alkyl with 1 to 5 carbon atoms or benzyl, —CONR'($R_1'$), wherein R' represents hydrogen, alkyl with 1 to 6 carbon atoms, hydroxyalkyl with 1 to 4 carbon atoms, alkoxyalkyl with 2 to 8 carbon atoms, phenyl or benzyl and $R_1'$ represents hydrogen, alkyl with 1 to 6 carbon atoms, hydroxyalkyl with 1 to 4 carbon atoms or alkoxyalkyl with 2 to 8 carbon atoms, or R' and $R_1'$ conjointly with the nitrogen represent a morpholino or piperidino radical, —$SO_2OR$, wherein R has the abovementioned meaning, —$SO_2NR'(R_1')$, wherein R' and $R_1'$ have the abovementioned meaning, alkyl-sulphonyl with 1 to 6 carbon atoms, benzylsulphonyl or unsubstituted phenylsulphonyl or phenylsulphonyl substituted by chlorine or methyl, or in the case of two substituents in the ortho-position, also alkylene with 3 to 4 carbon atoms or 1,3-butadienylene.

Within the framework of the formula (1), compounds of predominant interest are those of the formulae

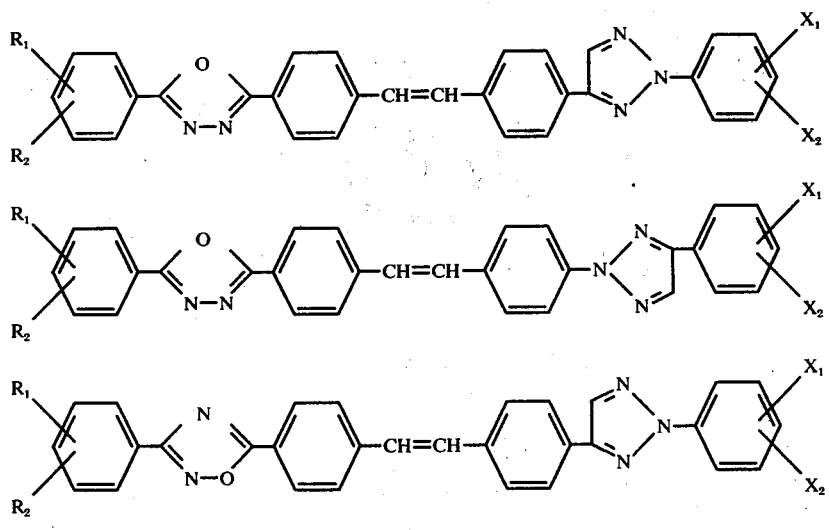

-continued and

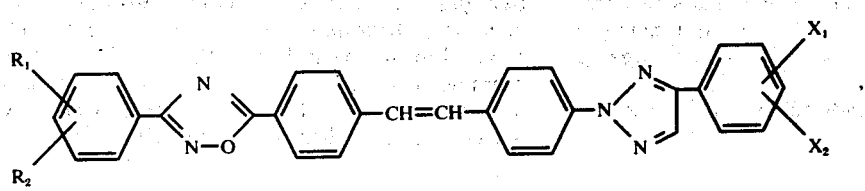
(7)

wherein $R_1$ denotes hydrogen, chlorine, alkyl with 1 to 4 carbon atoms, phenylalkyl with 1 to 3 carbon atoms in the alkyl part, phenyl or alkoxy with 1 to 4 carbon atoms, or $R_1$ conjointly with $R_2$ denotes a fused benzene radical, $R_2$ denotes hydrogen or methyl or $R_2$ conjointly with $R_1$ denotes a fused benzene radical, $X_1$ denotes hydrogen, alkyl with 1 to 4 carbon atoms, alkoxy with 1 to 4 carbon atoms, chlorine, carbalkoxy with 2 to 6 carbon atoms or alkylsulphonyl with 1 to 4 carbon atoms and $X_2$ denotes hydrogen, chlorine, methyl or methoxy.

Compounds of particular practical interest correspond to the formulae

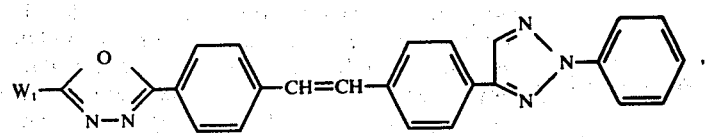
(8)

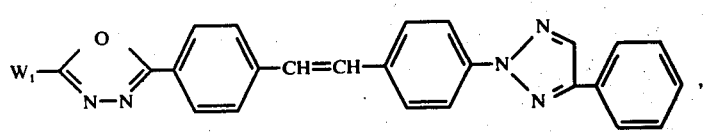
(9)

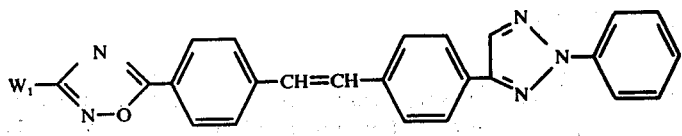
(10)

and

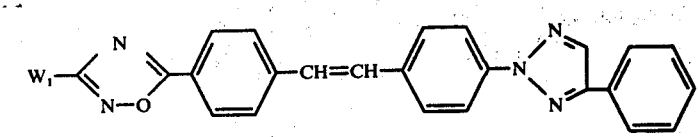
(11)

wherein $W_1$ denotes phenyl, m-methylphenyl, p-alkylphenyl with 2 to 4 C atoms in the alkyl part, m- and p-alkoxy-phenyl with 1 to 4 C atoms in the alkyl part, p-chlorophenyl, p-biphenylyl or naphthyl-(1).

Because of their easier accessibility, those amongst the compounds characterised by the above formulae in which not more than one of the R substituents in the terminal ring differs from hydrogen are to be singled out.

The compounds of the formulae (1) and (2) to (11) can be manufactured according to various processes.

One such new process, by means of which the new compounds can be manufactured, is characterised in that a methyl compound of the formula

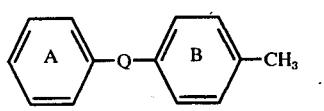
(12)

is reacted, in dimethylformamide as the reaction medium and in the presence of a strongly basic alkali metal compound, with a Schiff's base of the formula

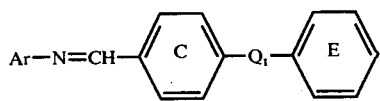
(13)

wherein Q, $Q_1$ and the rings A, B, C and E have the above-mentioned meaning and Ar denotes an aromatic radical, the reaction mixture initially being irradiated with UV light.

The irradiation, according to the invention, with UV light is effected by means of a source which is located either outside or inside the reaction vessel. In general, the irradiation with UV light is required only in order to start the reaction and not constantly until the reaction between the reactants has gone to completion. Therefore, an irradiation time of a few minutes is usually sufficient. Preferably, UV light with a wavelength of about 300 nm is used.

In general, the symbol Ar represents an optionally substituted naphthyl or, in particular, phenyl radical. Preferably, Ar represents the radical of the formula

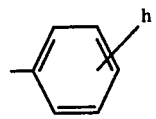
(14)

wherein $h$ denotes hydrogen or chlorine.

The strongly basic alkali metal compound used is generally such a compound of the formula $$MOC_{n-1}H_{2n-1} \quad (15)$$

wherein M denotes potassium or sodium and $n$ denotes an integer from 1 to 6.

Examples of compounds of the formula (15) which may be mentioned are sodium methylate, potassium tertiary butylate, sodium hydroxide and potassium hydroxide.

In the case of alcoholates, the reaction must be carried out in a virtually anhydrous medium, whilst in the case of the hydroxides, water contents of up to 25% are permissible. In the case of potassium hydroxide, which is preferably to be used, a water content of up to about 15% has proved suitable.

Appropriately, the compound containing methyl groups and the Schiff's bases are reacted in equivalent amounts so that neither component is present in a substantial excess. Advantageously, at least the equivalent amount of the alkali metal compound is used, that is to say at least 1 mol of alkali metal compound per mol of Schiff's base. When potassium hydroxide is used, two to eight times the equivalent amount are preferably employed.

The reaction according to the invention can be carried out at temperatures in the range between about 10° and 40° C. If potassium hydroxide is used for the reaction, the reaction generally already takes place at room temperature, in which case it is not necessary to supply heat from outside. When other alkali metal compounds are used the reaction must be carried out at elevated temperatures, depending on the base strength of these compounds. However, a reaction temperature which is as low as possible is desirable, since at higher temperatures side reactions, such as, for example, opening of the ring, can occur.

The end products can be worked up from the reaction mixture according to customary methods which are in themselves known.

Compounds of the formulae (2) to (11) are manufactured analogously, for example compounds of the formula (2) are manufactured by reacting a methyl compound of the formula

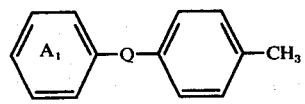
(16)

with a Schiff's base of the formula

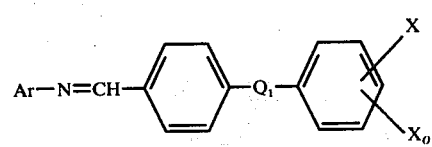
(17)

wherein the ring $A_1$ denotes a radical of the formula

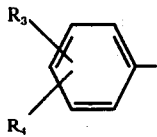 (18)

wherein $R_3$ represents hydrogen, m-methyl, alkyl with 2 to 12 carbon atoms, cyclohexyl, phenylalkyl with 1 to 3 carbon atoms in the alkyl part, phenyl which is optionally substituted by 1 to 2 substituents from the series chlorine or methoxy, alkoxy with 1 to 4 carbon atoms, phenoxy which is optionally substituted by 1 to 2 substituents from the series chlorine, methyl or methoxy, chlorine, bromine, —COOR, wherein R represents hydrogen, alkyl with 1 to 5 carbon atoms or benzyl, —CONR″($R_1'$) wherein R″ represents hydrogen, alkyl with 1 to 6 carbon atoms, hydroxyalkyl with 1 to 4 carbon atoms, alkoxyalkyl with 2 to 8 carbon atoms, phenyl or benzyl and $R_1'$ represents hydrogen, alkyl with 1 to 6 carbon atoms, hydroxyalkyl with 1 to 4 carbon atoms or alkoxyalkyl with 2 to 8 carbon atoms, or R″ and $R_1'$ conjointly with the nitrogen represent a morpholino or piperidino radical, —SO$_2$NR″($R_1'$), wherein R″ and $R_1'$ have the abovementioned meaning, alkylsulphonyl with 3 to 6 carbon atoms or phenylsulphonyl which is optionally substituted by chlorine, or $R_3$ conjointly with $R_4$ represents alkylene with 3 or 4 carbon atoms and $R_4$ represents hydrogen, alkyl with 2 to 5 carbon atoms or alkoxy with 1 to 4 carbon atoms, or $R_4$ conjointly with $R_3$ represents alkylene with 3 or 4 carbon atoms and X represents hydrogen, alkyl with 2 to 4 carbon atoms, cyclohexyl, phenylalkyl with 1 to 3 carbon atoms in the alkyl part, phenyl, alkoxy with 1 to 4 carbon atoms, phenoxy, chlorine, fluorine, alkylsulphonyl with 1 to 6 carbon atoms, benzylsulphonyl or phenylsulphonyl which is optionally substituted by chlorine or methyl. $X_0$ denotes hydrogen, chlorine, m-methyl or methoxy and $Q_1$ has the above-mentioned meaning.

The starting materials of the formulae (12) and (13) and (16) and (17) are known or are obtained analogously to processes which are in themselves known.

Another process, which is in itself known, for the manufacture compounds of the formula (1) is to react a compound of the formula

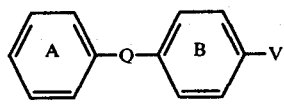 (19)

with a compound of the formula

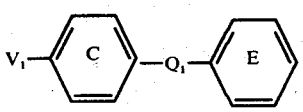 (20)

wherein Q, $Q_1$ and the rings A, B, C and E have the above-mentioned meaning and one of the symbols V and $V_1$ denotes a

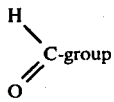

and the other denotes a grouping of the formula

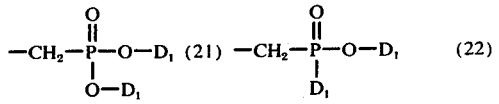

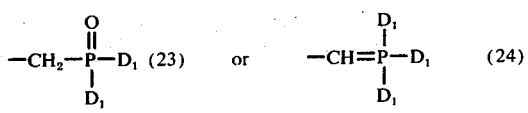

wherein $D_1$ represents an alkyl radical which is optionally further substituted, preferably an alkyl radical with up to 6 carbon atoms, an aryl radical, preferably a phenyl radical, a cycloalkyl radical, preferably a cyclohexyl radical, or an aralkyl radical, preferably a benzyl radical.

Advantageously, this manufacturing process is carried out in inert solvents. Examples of solvents which may be mentioned are hydrocarbons, such as toluene and xylene, or alcohols, such as methanol, ethanol, isopropanol or butanol, glycols, glycol ethers, such as 2-methoxy-ethanol, hexanols, cyclohexanol and cyclooctanol and also ethers, such as diisopropyl ether, tetrahydrofurane and dioxane, as well as dimethylsulphoxide, formamide and N-methylpyrrolidone. Polar organic solvents, such as dimethylformamide and dimethylsulphoxide, are particularly suitable. Some of the reactions can also be carried out in aqueous solution.

The temperature at which the reaction is carried out can vary within wide limits. It is determined α. by the stability of the solvent used towards the reactants, especially towards the strongly basic alkali metal compounds, β. by the reactivity of the compounds taking part in the condensation reaction and Γ. by the activity of the combination of solvent and base as the condensing agent.

Accordingly, temperatures between about 10° and 100° C can generally be used in practice, especially if dimethylformamide or dimethylsulphoxide is used as the solvent. The preferred temperature range is from 20° to 60° C.

Strongly basic alkali metal compounds which can be used are, above all, the hydroxides, amides and alcoholates (preferably those of primdry alcohols containing 1 to 4 carbon atoms) of the alkali metals, those of lithium, sodium and potassium being of predominant interest for economic reasons. However, in principle and in particular cases, alkali metal sulphides and alkali metal carbonates, aryl-alkali metal compounds, such as, for example, phenyllithium, or strongly basic amines (including ammonium bases, for example trialkylammonium hydroxides) can also be used successfully.

The new compounds defined above show a more or less pronounced fluorescence in the dissolved or finely divided state. They can be used for the optical brightening of the most diverse synthetic, semi-synthetic or natural organic materials or substances which contain such organic materials.

The following groups of organic materials, where optical brightening thereof is relevant, may be mentioned as examples of the above, without the survey given below being intended to express any restriction thereto:

I. Synthetic organic high molecular materials:

a. Polymerisation products based on organic compounds containing at least one polymerisable carbon-carbon double bond, that is to say their homopolymers or copolymers as well as their after-treatment products such as, for example, cross-linking, grafting or degradation products, polymer blends or products obtained by modification of reactive groups, for example polymers based on $\alpha,\beta$-unsaturated carboxylic acids or derivatives of such carboxylic acids, especially on acrylic compounds (such as, for example, acrylic esters, acrylic acid, acrylonitrile, acrylamides and their derivatives or their methacrylic analogues), on olefine hydrocarbons (such as, for example, ethylene, propylene, styrenes or dienes and also so-called ABS polymers), and polymers based on vinyl and vinylidene compounds (such as, for example, vinyl chloride, vinyl alcohol and vinylidene chloride), b. Polymerisation products such as are obtainable by ring opening, for example polyamides of the polycaprolactam type, and also polymers which are obtainable both via polyaddition and via polycondensation, such as polyethers or polyacetals, c. Polycondensation products or precondensates based on bifunctional or polyfunctional compounds possessing condensable groups, their homocondensation and co-condensation products, and after-treatment products, such as, for example, polyesters, especially saturated (for example ethylene glycol terephthalic acid polyester) or unsaturated (for example maleic acid-dialcohol polycondensates as well as their crosslinking products with copolymerisable vinyl monomers), unbranched and branched (also including those based on polyhydric alcohols, such as, for example, alkyd resins) polyesters, polyamides (for example hexamethylenediamine adipate), maleate resins, melamine resins, their precondensates and analogues, polycarbonates and silicones, and d. Polyaddition products such as polyurethanes (cross-linked and non-crosslinked) and epoxide resins.

II. Semi-synthetic organic materials, for example cellulose esters of varying degrees of esterification (so-called 2½-acetate or triacetate) or cellulose ether, regenerated cellulose (viscose or cuprammonium cellulose), or their after-treatment products, and casein plastics.

III. Natural organic materials of animal or vegetable origin, for example based on cellulose or proteins, such as cotton, wool, linen, silk, natural lacquer resins, starch and casein.

The organic materials to be optically brightened can be in the most diverse states of processing (raw materials, semi-finished goods or finished goods). On the other hand, they can be in the form of structures of the most diverse shapes, say for example predominantly three-dimensional bodies such as sheets, profiles, injection mouldings, various machined articles, chips, granules or foams, and also as predominantly two-dimensional bodies such as films, foils, lacquers, coatings, impregnations and coverings, or as predominantly one-dimensional bodies such as filaments, fibres, flocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fibre materials can, for example, be in the form of continuous filaments (stretched or unstretched), staple fibres, flocks, hanks, textile filaments, yarns, threads, fibre fleeces, felts, waddings, flocked structures or woven textile fabrics, textile laminates, knitted fabrics and papers, cardboards or paper compositions.

The compounds to be used according to the invention are of importance, inter alia, for the treatment of organic textile materials, especially woven textile fabrics. Where fibres, which can be in the form of staple fibres or continuous filaments or in the form of hanks, woven fabrics, knitted fabrics, fleeces, flocked substrates or laminates, are to be optically brightened according to the invention, this is advantageously effected in an aqueous medium, wherein the compounds in question are present in a finely divided form (suspensions, so-called microdispersions or possibly solutions). If desired, dispersing agents, stabilisers, wetting agents and further auxiliaries can be added during the treatment.

Depending on the type of brigtener compound used, it may prove advantageous to carry out the treatment in a neutral or alkaline or acid bath. The treatment is usually carried out at temperatures of about 20° to 140° C, for example at the boiling point of the bath or near it (about 90° C). Solutions or emulsions in organic solvents can also be used for the finishing, according to the invention, of textile substrates, as is practised in the dyeing trade in so-called solvent dyeing (pad-thermofix application, or exhaustion dyeing process in dyeing machines).

The new optical brighteners according to the present invention can further be added to, or incorporated in, the materials before or during their shaping. Thus, they can, for example, be added to the compression moulding composition or injection moulding composition during the manufacture of films, sheets (for example, hot milling into polyvinyl chloride) or mouldings.

Where fully synthetic or semi-synthetic organic materials are being shaped by spinning processes or via spinning compositions, the optical brighteners can be applied in accordance with the following processes:

Addition to the starting substances (for example monomers) or intermediates (for example precondensates or prepolymers), that is to say before or during the polymerisation, polycondensation or polyaddition, Powdering onto polymer chips or granules for spinning compositions, Bath dyeing of polymer chips or granules for spinning compositions, Metered addition to spinning melts or spinning solutions, and Application to the tow before stretching.

The new optical brighteners according to the present invention can, for example, also be employed in the following use forms:

a. Mixed with dyestuffs (shading) or pigments (coloured pigments or especially, for example, white pigments), or as an additive to dye baths, printing pastes, discharge pastes or reserve pastes, and furthermore for the after-treatment of dyeings, prints or discharge prints, b. Mixed with so-called "carriers", wetting agents, plasticisers, swelling agents, anti-oxidants, light protection agents, heat stabilisers and chemical bleaching agents (chlorite bleach or bleaching bath additives), c. Mixed with crosslinking agents or finishing agents (for example starch or synthetic finishes), and in combination with the most diverse textile finishing processes, especially synthetic resin finishes (for example creaseproof finishes such as "wash-and-wear", "permanent-press" or "no-iron"), as well as flameproof finishes, soft handle finishes, anti-soiling finishes or anti-static finishes, or antimicrobial finishes, d. Incorporation of the optical brighteners into polymeric carriers (polymerisation, polycondensation or polyaddition products), in a dissolved or dispersed form, for use, for example, in coating agents, impregnating agents or binders (solutions, dispersions and emulsions) for textiles, fleeces paper and leather, e. As additives to so-called "master batches", f. As additives to the most diverse industrial products in order to render these more marketable (for example improving the appearance of soaps, detergents and pigments), g. In combination with other optically brightening substances, h. In spinning bath preparations, that is to say as additives to spinning baths such as are used for improving the slip for the further processing of synthetic fibres, or from a special bath before the stretching of the fibre, i. As scintillators for various purposes of a photographic nature, such as, for example, for electrophotographic reproduction or supersensitisation, and for the optical brightening of photographic layers, optionally in combination with white pigments such as, for example, $TiO_2$, and k. Depending in each case on the subsitution, as laser dyestuffs.

If the brightening process is combined with textile treatment methods or finishing methods, combined treatment can in many cases advantageously be carried out with the aid of appropriate stable preparations, which contain the optically brightening compounds in such concentration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to follow in optically brightening a series of fibre substrates, for example of polyester fibres, with the brighteners according to the invention is to impregnate these fibres with the aqueous dispersions (or optionally also solutions) of the brighteners at temperatures below 75° C, for example at room temperature, and to subject them to dry heat treatment at temperatures above 100° C, it being generally advisable additionally to dry the fibre material beforehand at a moderately elevated temperature, for example at not less than 60° C and up to about 130° C. The heat treatment in the dry state is then advantageously carried out at temperatures between 120° and 225° C, for example by heating in a drying chamber, by ironing within the specified temperature range or by treatment with dry, superheated steam. The drying and dry heat treatment can also be carried out in immediate succession or be combined in a single process stage.

The amount of the new optical brighteners, to be used according to the invention, relative to the material to be optically brightened, can vary within wide limits. A distinct and durable effect is already achievable with very small amounts, in certain cases, for example, amounts of 0.0001 per cent by weight. However, amounts of up to about 0.8 per cent by weight and optionally of up to about 2 per cent by weight can also be employed. For most practical purposes, amounts between 0.0005 and 0.5 per cent by weight are of preferred interest.

The new optical brighteners are also particularly suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents in any stage of the manufacturing process of the washing agents, for example to the so-called "slurry" before spray-drying to the washing powder, or during the preparation of liquid washing agent combinations. They can be added either in the form of a solution or dispersion in water or other solvents or, without auxiliaries, as a dry brightening powder. For example, the brightening agents can be mixed, kneaded or ground with the detergent substances and, in this form, admixed to the finished washing powder. However, they can also be sprayed in a dissolved or predispersed form onto the finished washing agent.

Possible washing agents are the known mixtures of detergent substances such as, for example, soap in the form of chips and powders, synthetics, soluble salts of sulphonic acid half-esters of higher fatty alcohols, arylsulphonic acids with higher and/or multiple alkyl substituents, sulphocarboxylic acid esters of medium to higher alcohols, fatty acid acylaminoalkyl or acylaminoaryl-glycerol sulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other "soil redeposition inhibitors", and also alkali metal silicates, alkali metal carbonates, alkali metal borates, alkali metal perborates, nitrilotriacetic acid, ethylenediaminetetraacetic acid, and foam stabilisers such as alkanolamides of higher fatty acids. The washing agents can further contain, for example: antistatic agents, skin protection agents which restore fat, such as lanolin, enzymes, antimicrobial agents, perfumes and dyestuffs.

The new optical brighteners have the particular advantage that they are also active in the presence of active chlorine donors such as, for example, hypochlorite, and can be used without significant loss of the effects in wash liquors containing non-ionic washing agents, for example alkylphenol polyglycol ethers.

The compounds according to the invention are added in amounts of 0.005–1% or more, relative to the weight of the liquid or pulverulent finished washing agent. Wash liquors which contain the indicated amounts of the optical brighteners claimed impart a brilliant appearance in daylight when used to wash textiles of cellulose fibres, polyamide fibres, cellulose fibres with a high quality finish, polyester fibres, wool and the like.

The washing treatment is carried out as follows, for example:

The textiles indicated are treated for 1 to 30 minutes at 20° to 100° C in a wash liquor which contains 1 to 10 g/kg of a built-up composite washing agent and 0.05 to 1%, relative to the weight of the washing agent, of the brightening agents claimed. The liquor ratio can be 1:3 to 1:50. After washing, the textiles are rinsed and dried in the usual manner. The wash liquor can contain 0.2 g/l of active chlorine (for example as hypochlorite) or 0.1 to 2 g/l of sodium perborate as a bleaching additive.

The compounds according to the invention are used in particular for the optical brightening of organic materials made of polyesters.

In the examples the parts, unless otherwise stated, are always parts by weight and the percentages are always percentages by weight. Unless otherwise noted, melting points and boiling points are uncorrected.

Manufacturing Instruction A 2.95 g (0.0125 mol) of 2-(p-tolyl)-5-phenyl-1,3,4-oxadiazole of the formula

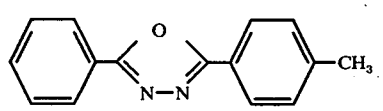
(101)

4.48 g (0.0125 mol) of the Schiff's base, obtained from 2-phenyl-4-(p-formylphenyl)-2H-1,2,3-triazole and o-chloroaniline of the formula

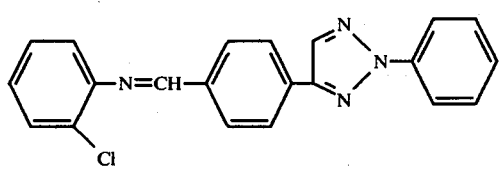
(102)

and 3.15 g (~ 0.05 mol) of powdered potassium hydroxide with a water content of about 10% are stirred in 80 ml of dimethylformamide for 1 hour at 20° to 25° C, under nitrogen. During the first 10 minutes of the reaction, the reaction vessel is irradiated with UV light of wavelengths above 300 nm. The colour of the reaction mixture gradually changes from yellow via red-brown to violet-blue. Thereafter, 400 ml of methanol are added and the mixture is cooled to 0° C. The reaction product which has precipitated is filtered off, washed with 70 ml of methanol and dried.

5.2 g (corresponding to 89.6% of theory) of 4-(5-phenyl-1,3,4-oxadiazol-2-yl)-4'-(2-phenyl-2H-1,2,3-triazol-4-yl)-stilbene of the formula

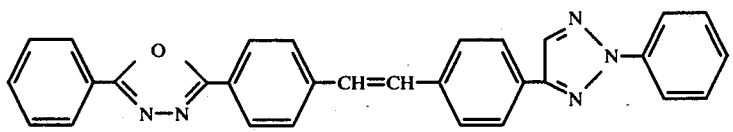
(103)

are obtained as a light grey powder of melting point 209° to 210° C. After recrystallising twice from o-dichloro-benzene (bleaching earth), 4.3 g (74.1% of theory) of small, almost colourless, shiny needles of melting point 210° to 211° C are obtained.

| Analysis: | $C_{30}H_{21}N_5O$ | (467.51) |
|---|---|---|
| | Calculated: | C 77.07 H 4.53 N 14.98% |
| | found: | C 76.79 H 4.48 N 14.95%. |

Manufacturing Instruction B 3.12 g (0.01 mol) of 2-(p-tolyl)-5-(p-biphenylyl)-1,3,4-oxadiazole of the formula

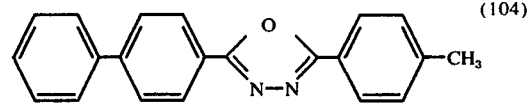
(104)

3.59 g (0.01 mol) of the Schiff's base, obtained from 2-(p-formylphenyl)-4-phenyl-2H-1,2,3-triazole and o-chloroaniline, of the formula

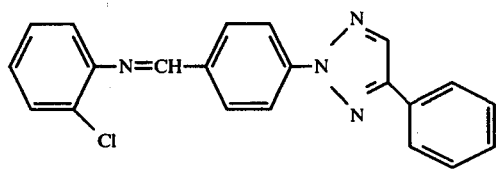
(105)

and 1.12 g (0.01 mol) of potassium t.-butylate are stirred in 100 ml of dimethylformamide at 20° to 30° C for 40 minutes under nitrogen. During the first 10 minutes of the reaction, the reaction mixture is irradiated with UV light of wavelengths above 300 nm. Thereafter, 400 ml of methanol are added and the mixture is cooled to 0° C. The reaction product which has precipitated is filtered off, washed with 70 ml of methanol and dried. 4.63 g (corresponding to 85.3% of theory) of 4-[5-(p-biphenylyl)-1,3,4-oxadiazol-2-yl]-4'-(4-phenyl-2H-1,2,3triazol-2-yl)-stilbene of the formula

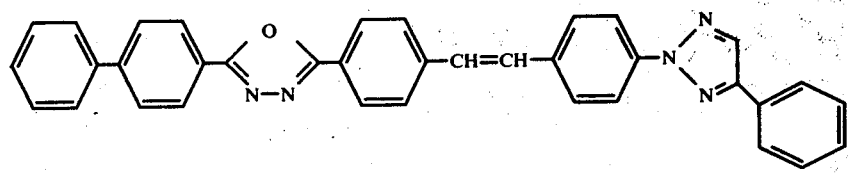

(106)

are obtained as a pale yellow powder of melting point 285° to 286° C. After recrystallising twice from o-dichlorobenzene (bleaching earth), 4.01 g (73.8% of theory) of small, pale greenish-tinged yellow, shiny flakes of melting point 287° to 288° C are obtained.

| Analysis: | $C_{36}H_{26}N_5O$ | (543.60) |
|---|---|---|
| | Calculated: | C 79.54 H 4.64 N 12.88% |

-continued

| Analysis: | $C_{36}H_{26}N_5O$ | (543.60) |
|---|---|---|
| | found: | C 79.46 H 4.83 N 12.87%. |

The stilbene compounds of the formulae (107), (115), (123) and (127), which are listed in the Tables I to IV, can be prepared according to one of the manufacturing instructions A or B.

Table I (107)

| No. | R | Instruction | Melting point: ° C |
|---|---|---|---|
| 108 | m-$C_6H_4CH_3$ | A | 221 – 222 |
| 109 | m-$C_6H_4OCH_3$ | A | 235 – 236 |
| 110 | p-$C_6H_4OCH_3$ | B | 216 – 217 |
| 111 | p-$C_6H_4Cl$ | B | 254 – 255 |
| 112 | p-$C_6H_4C(CH_3)_3$ | B | 235 – 236 |
| 113 | p-$C_6H_4C_6H_5$ | B | 269 – 270 |
| 114 | naphthyl-(1) | A | 247 – 248 |

Table II (115)

| No. | R | Instruction | Melting point: ° C |
|---|---|---|---|
| 116 | —$C_6H_5$ | A | 227 – 228 |
| 117 | m-$C_6H_4CH_3$ | A | 208 – 209 |
| 118 | m-$C_6H_4OCH_3$ | A | 188.5–189 |
| 119 | p-$C_6H_4OCH_3$ | B | 236 – 237 |
| 120 | p-$C_6H_4Cl$ | B | 280 – 281 |
| 121 | p-$C_6H_4C(CH_3)_3$ | B | 232 – 233 |
| 122 | naphthyl-(1) | B | 263 – 264 |

Table III (123)

| No. | R | Instruction | Melting point: ° C |
|---|---|---|---|
| 124 | H | A | 201 – 202 |
| 125 | Cl | A | 219 – 220 |
| 126 | $CH_3$ | A | 190.5 – 191 |

Table IV

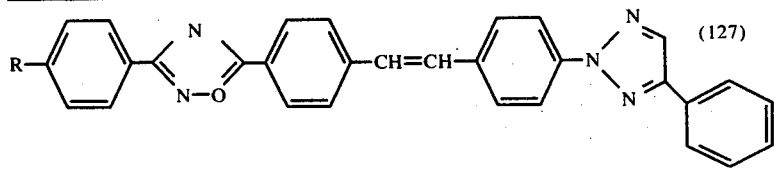

| No. | R | Instruction | Melting point: °C |
|---|---|---|---|
| 128 | H | A | 228 – 229 |
| 129 | Cl | A | 249 – 250 |
| 130 | CH₃ | A | 279 – 280 |

EXAMPLE 1

100 parts of polyester granules consisting of terephthalic acid ethylene glycol polyester are intimately mixed with 0.05 part of one of the compounds of the formulae (103), (106), (108) to (114), (116) to (122), (124) to (126) and (128) to (130) and the mixture is melted at 285° C whilst stirring. After the spinning melt has been spun out through customary spinnerets, strongly brightened polyester fibres of good fastness to light are obtained.

It is also possible to add the abovementioned compounds to the starting materials before or during the polycondensation to give the polyester.

EXAMPLE 2

A polyester fabric (for example "Dacron") is padded at room temperature (about 20° C) with an aqueous dispersion, which contains, per litre, 2 g of one of the compounds of the formulae (103), (106), (108) to (114), (116) to (122), (124) to (126) and (128) to (130) as well as 1 g of a product of the addition reaction of about 8 mols of ethylene oxide with 1 mol of p-tert.-octylphenol, and dried at about 100° C. The dry material is then subjected to a heat treatment at 170° to 220° C, the treatment time being 2 minutes down to a few seconds, depending on the temperature.

The material treated in this way shows a strong brightening effect with good fastness to light.

What we claim is:

1. Stilbene compounds of the fiormula

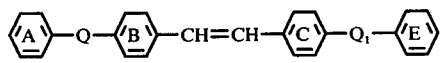

wherein

Q denotes the 1,3,4-oxadiazol-2,5-ylene or 1,2,4-oxadiazol-3,5-ylene radical and $Q_1$ denotes one of the radicals

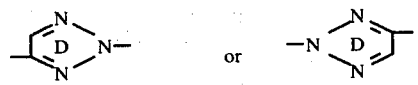

and the rings A, and E can each contain up to 2 non-chromophoric substituents.

2. Stilbene compounds according to claim 1, of the formula

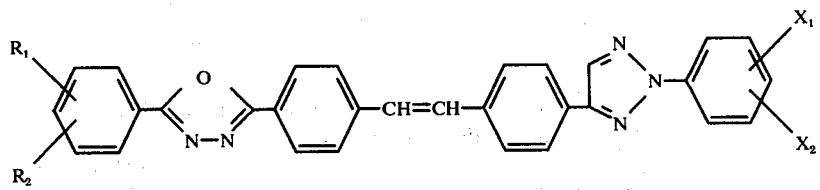

wherein $R_1$ denotes hydrogen, chlorine, alkyl with 1 to 4 carbon atoms, phenylalkyl with 1 to 3 carbon atoms in the alkyl part, phenyl or alkoxy with 1 to 4 carbon atoms, or $R_1$ conjointly with $R_2$ denotes a fused benzene radical, $R_2$ denotes hydrogen or methyl or $R_2$ conjointly with $R_1$ denotes a fused benzene radical, $X_1$ denotes hydrogen, alkyl with 1 to 4 carbon atoms, alkoxy with 1 to 4 carbon atoms, chlorine, carbalkoxy with 2 to 6 carbon atoms or alkylsulphonyl with 1 to 4 carbon atoms and $X_2$ denotes hydrogen, chlorine, methyl or methoxy.

3. Stilbene compounds according to claim 1, of the formula

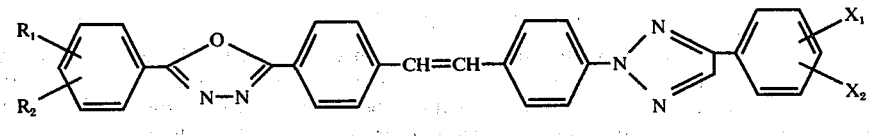

wherein $R_1$ denotes hydrogen, chlorine, chlorine, alkyl with 1 to 4 carbon atoms, phenylalkyl with 1 to 3 carbon atoms in the alkyl part, phenyl or alkoxy with 1 to 4 carbon atoms, or $R_1$ conjointly with $R_2$ denotes a fused benzene radical, $R_2$ denotes hydrogen or methyl or $R_2$ conjointly with $R_1$ denotes a fused benzene radical, $X_1$ denotes hydrogen, alkyl with 1 to 4 carbon atoms, alkoxy with 1 to 4 carbon atoms, chlorine, carbalkoxy with 2 to 6 carbon atoms or alkylsulphonyl with 1 to 4 carbon atoms and $X_2$ denotes hydrogen, chlorine, methyl or methoxy.

4. Stilbene compounds according to claim 1, of the formula

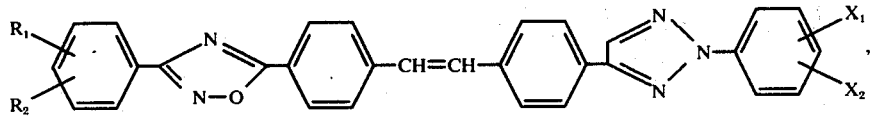

Wherein $R_1$ denotes hydrogen, chlorine, alkyl with 1 to 4 carbon atoms, phenylalkyl with 1 to 3 carbon atoms in the alkyl part, phenyl or alkoxy with 1 to 4 carbon atoms, or $R_1$ conjointly with $R_2$ denotes a fused benzene radical, $R_2$ denotes hydrogen or methyl or $R_2$ conjointly with $R_1$ denotes a fused benzene radical, $X_1$ denotes hydrogen, alkyl with 1 to 4 carbon atoms, alkoxy with 1 to 4 carbon atoms, chlorine, carbalkoxy with 2 to 6 carbon atoms or alkylsulphonyl with 1 to 4 carbon atoms and $X_2$ denotes hydrogen, chlorine, methyl or methoxy.

5. Stilbene compounds according to claim 1, of the formula

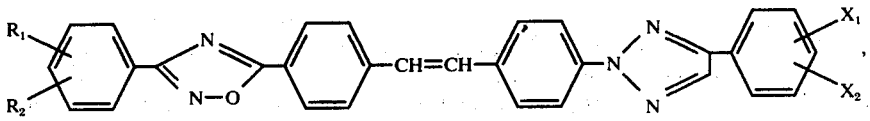

wherein $R_1$ denotes hydrogen, chlorine, alkyl with 1 to 4 carbon atoms, phenylalkyl with 1 to 3 carbon atoms in the alkyl part, phenyl of alkoxy with 1 to 4 carbon atoms, or $R_1$ conjointly with $R_2$ denotes a fused benzene radical, $R_2$ denotes hydrogen or methyl or $R_2$ conjointly with $R_1$ denotes a fused benzene radical, $X_1$ denotes hydrogen, alkyl with 1 to 4 carbon atoms, alkoxy with 1 to 4 carbon atoms, chlorine, carbalkoxy with 2 to 6 carbon atoms or alkylsulphonyl with 1 to 4 carbon atoms and $X_2$ denotes hydrogen, chlorine, methyl or methoxy.

6. Stilbene compounds according to claim 2, of the formula

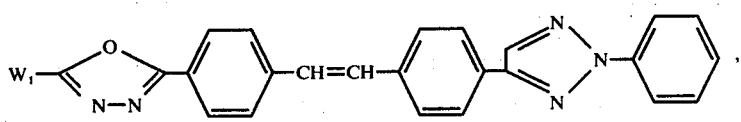

wherein $W_1$ denotes phenyl, m-methylphenyl, p-alkylphenyl with 2 to 4 C atoms in the alkyl part, m- and p-alkoxyphenyl with 1 to 4 C atoms in the alkyl part, p-chlorophenyl, p-biphenylyl or naphthyl-(1).

7. Stilbene compounds according to claim 3, of the formula

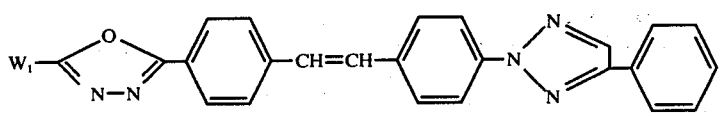

wherein $W_1$ denotes phenyl, m-methylphenyl, p-alkylphenyl with 2 to 4 C atoms in the alkyl part, m- and p-alkoxyphenyl with 1 to 4 C atoms in the alkyl part, p-chlorophenyl, p-biphenylyl or naphthyl-(1).

8. Stilbene compounds according to claim 4, of the formula

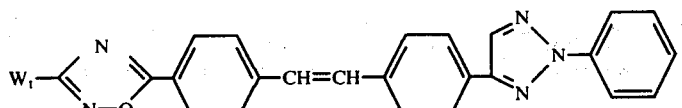

wherein $W_1$ denotes phenyl, m-methylphenyl, p-alkylphenyl with 2 to 4 C atoms in the alkyl part, m- and p-alkoxyphenyl with 1 to 4 C atoms in the alkyl part, p-chlorophenyl, p-biphenylyl or naphthyl-(1).

9. Stilbene compounds according to claim 5, of the formula

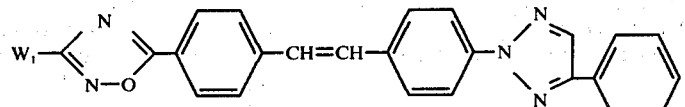

wherein $W_1$ denotes phenyl, m-methylphenyl, p-alkylphenyl with 2 to 4 C atoms in the alkyl part, m- and p-alkoxyphenyl with 1 to 4 C atoms in the alkyl part, p-chlorophenyl, p-biphenylyl or naphthyl-(1).

10. Stilbene compound according to claim 6, of the formula

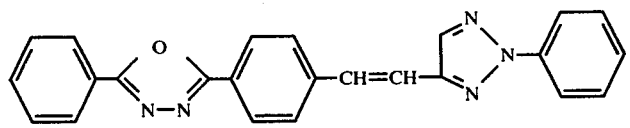

11. Stilbene compound according to claim 7, of the formula

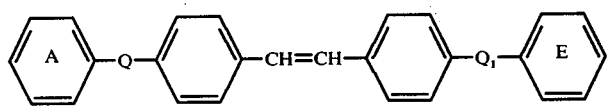

12. Stilbene compounds, according to claim 1 of the formula wherein

Q denotes the 1,3,4-oxadiazol-2,5-ylene or 1,2,4-oxadiazol-3,5-ylene radical and
Q₁ denotes one of the radicals or 

and the rings A and E can each contain 2 non-chromophoric substituents.

UNITED STATES PATENT OFFICE
CERTIFICATE OF CORRECTION

PATENT NO. : 4,014,871
DATED : March 29, 1977
INVENTOR(S) : GEZA KORMANY ET AL.

It is certified that error appears in the above–identified patent and that said Letters Patent are hereby corrected as shown below:

Col. 18, line 58, delete the second "chlorine".

Signed and Sealed this

Twenty-first Day of June 1977

[SEAL]

Attest:

RUTH C. MASON
Attesting Officer

C. MARSHALL DANN
Commissioner of Patents and Trademarks